United States Patent
Yonezawa

(10) Patent No.: US 6,928,185 B2
(45) Date of Patent: Aug. 9, 2005

(54) DEFECT INSPECTION METHOD AND DEFECT INSPECTION APPARATUS

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 611 days.

(21) Appl. No.: 09/895,204

(22) Filed: Jul. 2, 2001

(65) Prior Publication Data

US 2002/0001405 A1 Jan. 3, 2002

(30) Foreign Application Priority Data

Jun. 30, 2000 (JP) ................................. P. 2000-203067

(51) Int. Cl.⁷ ................................................ G06K 9/00
(52) U.S. Cl. ...................... 382/149; 382/141; 382/206; 382/298; 356/237.1; 348/125
(58) Field of Search .................. 382/141–152, 382/206, 298; 356/237.1; 348/125–134

(56) References Cited

U.S. PATENT DOCUMENTS

| | | | | |
|---|---|---|---|---|
| 4,845,558 A | * | 7/1989 | Tsai et al. | 348/126 |
| 4,926,452 A | * | 5/1990 | Baker et al. | 378/22 |
| 4,926,489 A | | 5/1990 | Danielson et al. | |
| 5,293,538 A | | 3/1994 | Iwata et al. | |
| 5,790,694 A | * | 8/1998 | Maruo | 382/149 |
| 5,864,394 A | | 1/1999 | Jordan, III et al. | |
| 5,907,628 A | | 5/1999 | Yolles et al. | |
| 5,995,137 A | * | 11/1999 | Yamada et al. | 348/88 |
| 6,148,097 A | * | 11/2000 | Nakayama et al. | 382/141 |
| 6,222,624 B1 | | 4/2001 | Yonezawa | 356/237.1 |
| 6,286,969 B1 | * | 9/2001 | Kurokawa et al. | 362/11 |
| 6,347,150 B1 | * | 2/2002 | Hiroi et al. | 382/149 |
| 6,529,622 B1 | * | 3/2003 | Pourjavid | 382/149 |
| 6,539,106 B1 | * | 3/2003 | Gallarda et al. | 382/149 |

FOREIGN PATENT DOCUMENTS

| | | | |
|---|---|---|---|
| EP | 0 930 498 A2 | 7/1999 | |
| JP | 7-209203 | 8/1995 | G01N/21/88 |

* cited by examiner

Primary Examiner—Bhavesh M. Mehta
Assistant Examiner—Aaron Carter
(74) Attorney, Agent, or Firm—Sughrue Mion, PLLC

(57) ABSTRACT

A defect inspection method of inspecting a defect of an inspection object having a chip pattern, the defect inspection method comprising the steps of: inputting a captured first image of the inspection object; obtaining a second image having a predetermined size based on one of a chip size and a size of exposure shot from the inputted first image; determining an averaged luminance of the obtained second image; and detecting the defect based on the determined averaged luminance and a predetermined inspection condition.

10 Claims, 7 Drawing Sheets

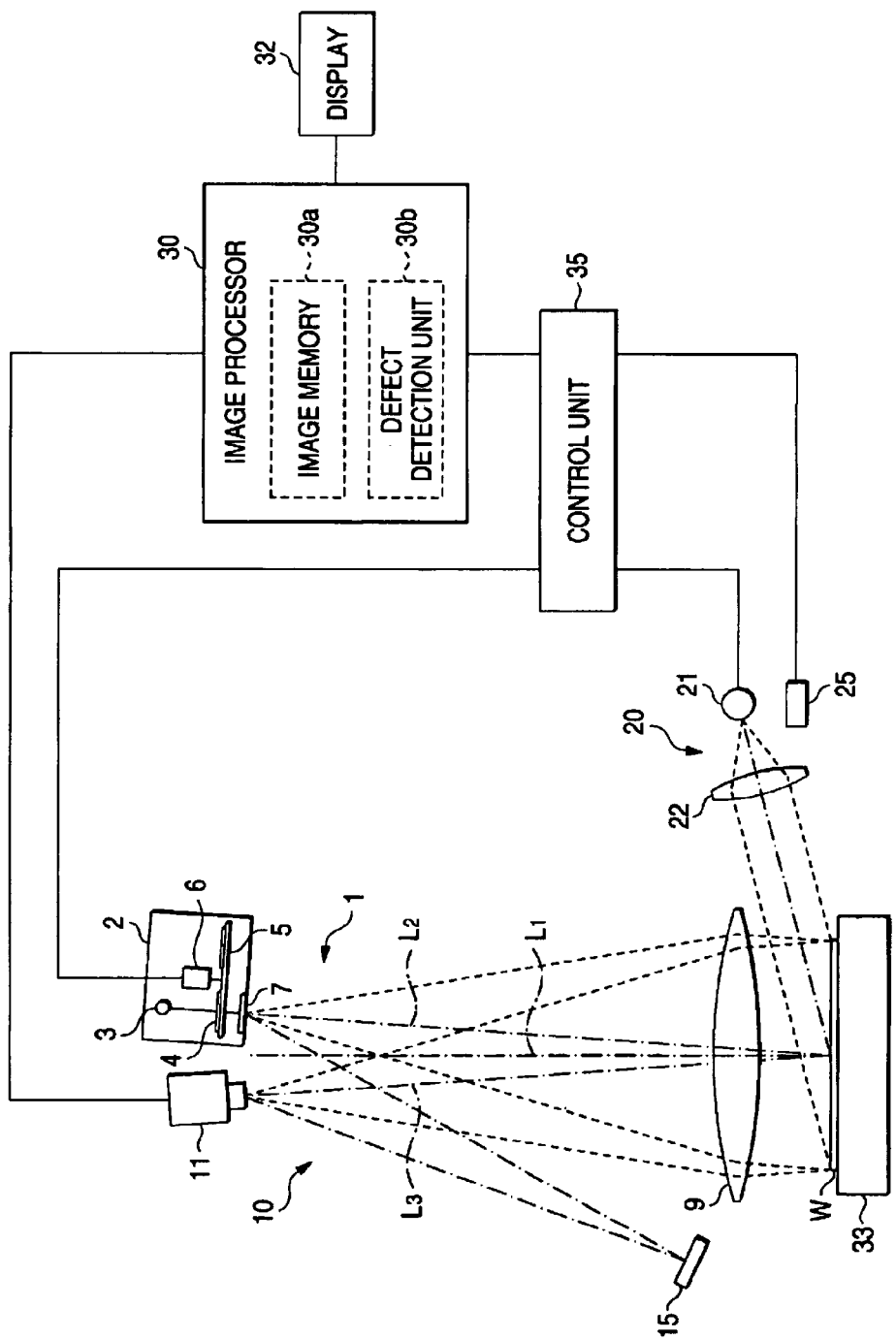

DEFECT INSPECTION METHOD AND DEFECT INSPECTION APPARATUS

BACKGROUND OF THE INVENTION

1. Technical Field of the Invention

The present invention relates to a defect inspection method for inspecting the presence or absence of a defect of an object to be inspected (inspection object) such as a semiconductor wafer having a chip pattern, as well as a defect inspection apparatus based on that method.

2. Related Art

For inspecting the presence or absence of a defect etc. on a semiconductor wafer surface where a chip pattern is formed, a method is known in which the presence or absence of a defect is inspected by making a comparison between a captured image of a wafer as the inspection object and a master image of a wafer having no defect.

However, in an apparatus for inspecting a defect through the comparison with the master image, it is necessary to register master images individually for every apparatus, so that the amount of operation for that purpose increases. In addition, in a case where an optical system for capturing the image of the wafer is adjusted, it is necessary to re-register the master image as well, which takes a lot of trouble in the practical operation.

SUMMARY OF THE INVENTION

In view of the above-described problems of the related art, it is an object of the invention to provide a defect inspection method for permitting high-speed inspection without using a master image, as well as a defect inspection apparatus based on that method.

To achieve the above problems, according to a first aspect of the invention, there is provided a defect inspection method of inspecting a defect of an inspection object having a chip pattern, the defect inspection method comprising the steps of:

inputting a captured first image of the inspection object;

obtaining a second image having a predetermined size based on one of a chip size and a size of exposure shot from the inputted first image;

determining an averaged luminance of the obtained second image; and detecting the defect based on the determined averaged luminance and a predetermined inspection condition.

According to a second aspect of the invention, in the defect inspection method of the first aspect, the obtaining step includes steps of converting the inputted first image to a third image so that a first size of an integral multiple of the chip size is a second size of a substantially integral multiple of a size of a pixel, and generating an averaged image as the second image by averaging the converted third image, the generated averaged image having the second size, the determining step includes a step of determining a luminance of the generated averaged image as the averaged luminance, and the detecting step includes a step of detecting the defect based on the determined luminance of the generated averaged image and a predetermined reference luminance as the predetermined inspection condition.

According to a third aspect of the invention, in the defect inspection method of the first aspect, the obtaining step includes steps of extracting third images of each exposure shot from the inputted first image, generating an average shot image by averaging the extracted third images, and extracting fourth images at four corners of the generated average shot image each of which has a first size smaller than a size of the exposure shot, the extracted fourth images being as the second image, the determining step includes a step of determining an averaged luminance of each fourth image, respectively, and the detecting step includes steps of determining a difference in the determined averaged luminance between two of the fourth images which are in diagonal position, and detecting the defect based on the determined difference in the averaged luminance and a predetermined reference luminance difference as the predetermined inspection condition.

According to a fourth aspect of the invention, in the defect inspection method of the third aspect, the first size includes one of a size of an integral multiple of the chip size and a size of substantially ⅓ to ½ of the size of the exposure shot.

According to a fifth aspect of the invention, in the defect inspection method of the first aspect, the obtaining step includes steps of extracting third images of each exposure shot from the inputted first image, generating an average shot image by averaging the extracted third images, and generating an averaged image as the second image by averaging the generated average shot image, the generated averaged image having a first size smaller than the size of the exposure shot, the determining step includes a step of determining a luminance of the generated averaged image as the averaged luminance, and the detecting step includes steps of determining degree of variation of the determined luminance, and detecting the defect based on the determined degree of the variation of the luminance and a predetermined reference luminance variation degree as the predetermined inspection condition.

According to a sixth aspect of the invention, in the defect inspection method of the fifth aspect, the first size includes one of a size of an integral multiple of the chip size and a size of substantially ⅓ to ½ of the size of the exposure shot.

According to a seventh aspect of the invention, the defect inspection method of the first aspect further comprising the steps of: illuminating the inspection object with a substantially parallel illumination light; capturing the image of the inspection object; detecting a luminance of the illumination light; and adjusting the luminance of the illumination light based on the detection result in the detecting step.

To achieve the above problems, according to an eighth aspect of the invention, there is provided a defect inspection apparatus for inspecting a defect of an inspection object having a chip pattern, the defect inspection apparatus comprising:

an inputting unit which inputs a captured first image of the inspection object; and an image processor which detects the defect according to a program stored therein, the program including the steps of, obtaining a second image having a predetermined size based on one of a chip size and a size of an exposure shot from the inputted first image, determining an averaged luminance of the obtained second image, and detecting the defect based on the determined averaged luminance and a predetermined inspection condition.

To achieve the above problems, according to a ninth aspect of the invention, there is provided a defect inspection apparatus for inspecting a defect of an inspection object having a chip pattern, the defect inspection apparatus comprising:

an inputting unit which inputs a captured first image of the inspection object; and an image processor which detects the defect according to a program stored therein, the program including the steps of, converting the inputted first image to a second image so that a first size of an integral multiple of the chip size is a second size of a substantially integral multiple of a size of a pixel, generating an averaged image having the second size by averaging the converted second image, determining a luminance of the generated averaged image, and detecting the defect based on the determined luminance of the generated averaged image and a predetermined reference luminance.

To achieve the above problems, according to a tenth aspect of the invention, there is provided a defect inspection apparatus for inspecting a defect of an inspection object having a chip pattern, the defect inspection apparatus comprising:

an inputting unit which inputs a captured first image of the inspection object; and an image processor which detects the defect according to a program stored therein, the program including the steps of, extracting second images of each exposure shot from the inputted first image, generating an average shot image by averaging the extracted second images, extracting third images at four corners of the generated average shot image each of which has a first size smaller than a size of the exposure shot, determining an averaged luminance of each third image respectively, determining a difference in the determined averaged luminance between two of the third images which are in diagonal position, and detecting the defect based on the determined difference in the averaged luminance and a predetermined reference luminance difference.

According to an eleventh aspect of the invention, in the defect inspection apparatus of the tenth aspect, the first size includes one of a size of an integral multiple of the chip size and a size of substantially ⅓ to ½ of the size of the exposure shot.

To achieve the above problems, according to a twelfth aspect of the invention, there is provided a defect inspection apparatus for inspecting a defect on an inspection object having a chip pattern, the defect inspection apparatus comprising:

an inputting unit which inputs a captured first image of the inspection object; and an image processor which detects the defect according to a program stored therein, the program including the steps of, extracting second images of each exposure shot from the inputted first image, generating an average shot image by averaging the extracted second images, generating a averaged image by averaging the generated average shot image, the generated averaged image having a first size smaller than the size of the exposure shot, determining a luminance of the generated averaged image, determining degree of variation of the determined luminance, and detecting the defect based on the determined degree of variation of the luminance and a predetermined reference luminance variation degree.

According to a thirteenth aspect of the invention, in the defect inspection apparatus of the twelfth aspect, the first size includes one of a size of an integral multiple of the chip size and a size of substantially ⅓ to ½ of the size of the exposure shot.

According to a fourteenth aspect of the invention, the defect inspection apparatus of the eighth aspect further includes: an illuminating optical system which illuminates the inspection object with a substantially parallel illumination light;

an imaging optical system which captures the first image of the inspection object;

a detector which detects a luminance of the illumination light; and a controller which adjusts the luminance of the illumination light based on the detection result by the detector.

BRIEF DESCRIPTION OF THE DRAWINGS

FIG. 1 is a schematic diagram of a defect inspection apparatus in accordance with an embodiment of the invention;

DETAILED DESCRIPTION OF PREFERRED EMBODIMENT

Figure 2A:
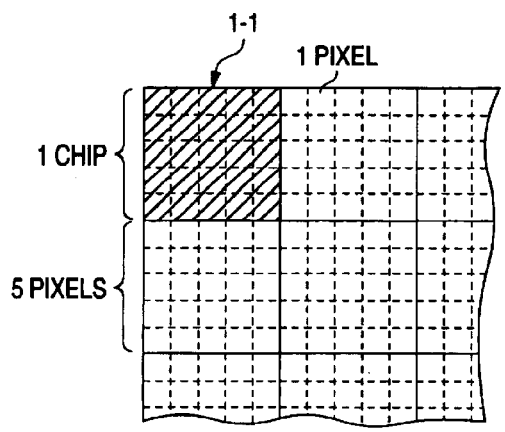
FIGS. 2A to 2D are a diagram explaining the averaging processing of a first defect inspection.

Referring now to the drawings, a description will be given of an embodiment of the invention. FIG. 1 is a schematic diagram of a defect inspection apparatus in accordance with an embodiment of the invention.

Reference numeral 1 denotes a bright-field illuminating optical system for illuminating a wafer W which is an object to be inspected (inspection object) placed on an X-Y stage. The bright-field illuminating optical system 1 has an illumination unit 2 and a collimator lens 9 having a diameter larger than that of the inspection surface (surface) of the wafer W. The illumination unit 2 includes a halogen lamp 3 which is a light source, a rotating plate 5 having a plurality of wavelength selection filters 4 and an opening for white illumination, a motor 6 for rotating the rotating plate 5, and a diffusion plate 7. The filters 4 are used for selectively converting the white illumination light emitted from the lamp 3 into narrow-band light having different central wavelengths, and are provided to change the central wavelengths of the narrow-band light at predetermined intervals.

The rotating plate 5 is rotated by the motor 6, so that a desired filter 4 or the opening is selectively disposed in the optical path of the illumination light. The illumination light passed through the filter 4 or the opening is diffused by the diffusion plate 7 and is converted into diffused illumination light with sufficiently uniform luminance. The diffused illumination light is converted into substantially parallel light by the lens 9, and then illuminates the wafer W placed on the stage 33.

Reference numeral 20 denotes a dark-field illuminating optical system having a light source 21 such as a halogen lamp and a lens 22. The light source 21 is disposed in the vicinity of the front-side focal point of the lens 22. The illumination light emitted from the light source 21 is converted into substantially parallel light by the lens 22, and then illuminates the overall surface of the wafer W from a diagonal direction.

Reference numeral 10 denotes an imaging optical system for imaging the wafer W, and the imaging optical system 10 has the collimator lens 9 used jointly with the bright-field illuminating optical system 1, and a CCD camera 11. An image formation optical system of the camera 11 is disposed in the vicinity of the focal point of the lens 9, and is capable of imaging the overall surface of the wafer W from the substantially identical direction. An optical axis L3 of the imaging optical system 10 is disposed so as to be symmetrical to an optical axis L2 of the bright-field illuminating optical system 1 with respect to an optical axis L1 of the lens 9 placed therebetween. Further, the camera 11 is placed at a position for imaging the wafer W from a substantially vertical direction while avoiding the interference with the illumination unit 2. In this embodiment, each of the angle formed by the optical axis L1 and the optical axis L2 and the angle formed by the optical axis L1 and the optical axis L3 is set to be 3 degrees (since the inclination of the optical axis L3 with respect to the inspection surface of the wafer W is not very large, the distortion of the image and the effect of defocusing are small).

The lens 9 converges the regular reflection from the wafer W illuminated by the bright-field illuminating optical system 1, and an imaging element of the camera 11 collectively forms an image of a substantially entire surface of the wafer W. On the other hand, the lens 9 similarly converges the scattered reflection from the wafer W illuminated by the dark-field illuminating optical system 20, and the imaging element of the camera 11 forms the image.

A mirror 15 is disposed at a position which is in the vicinity of the lens 9 and offset from the respective optical paths of the bright-field illuminating optical system 1 and the imaging optical system 10. The mirror 15 reflects the illumination light emitted from the illumination unit 2 toward the imaging surface of the camera 11. The camera 11 is jointly used as a detector for monitoring (detecting) the quantity of the illumination light for bright-field illumination.

On the other hand, a light quantity sensor 25 is disposed in the vicinity of the light source 21 of the dark-field illuminating optical system 20 so as to monitor (detect) the quantity of the illumination light of the light source 21. It should be noted that, with respect to the configuration of the light quantity monitor (detection) for dark-field illumination, by disposing a scattering plate on the placing surface of the stage 33 where the wafer W is placed, it is also possible to use the camera 11 for monitoring (detecting) the quantity of the illumination light for dark-field illumination in the same way as with the bright-field illumination.

It should be noted that the rotating plate 5 having the filters 4 etc. may be disposed on the imaging optical system 10 side. Further, the wavelength may be varied by using a monochrometer instead of the wavelength selection filters.

Image data representing the image of the wafer W from the camera 11 is inputted to an image processor 30 having an image memory 30a for storing the image data and a defect detection unit 30b. A display 32 for displaying information such as the results of inspection and a control unit 35 are connected to the image processor 30. The illumination unit 2, the light source 21, and the sensor 25 are connected to the control unit 35.

The camera 11 is disposed at a position where it is able to image all the positions of the wafer W in the same direction and image the entire surface of the wafer W under the same optical conditions. However, shading occurs in the captured image depending on the lens characteristics of the lens 9 and the camera 11. As a measure against this problem, the image processor 30 prepares in advance a correction coefficient image by measuring the luminance distribution, and performs a correction by subjecting the prepared image to multiplication processing. This correction is performed for each of the captured image by the bright-field illumination and the captured image by the dark-field illumination. In the case where imaging is effected by selectively changing the wavelength of the illumination in bright-field illumination (in the case of a defect having a wavelength characteristic, the defect can be easily detected by changing the wavelength of the illumination light), the correction of the luminance is performed with respect to each wavelength.

In addition, if the quantity of illumination light changes, the reliability of the image is affected, so that the following procedure is taken. The control unit 35 obtains through the image processor 30 a signal representative of the quantity of the bright-field illuminating light monitored (detected) by the camera 11. Then, the control unit 35 adjusts the quantity of light of the halogen lamp 3. In addition, upon receipt of the signal from the sensor 25, the control unit 35 adjusts the quantity of light of the light source 21 through a lamp driver (not illustrated).

Through the above-described procedure, it is possible to optimize the quantity of light of the image captured by the camera 11. It should be noted that the image captured with a fixed quantity of light can be obtained by adjusting the shutter speed of the camera 11 apart from the adjustment of the quantity of illumination light.

Figure 5:
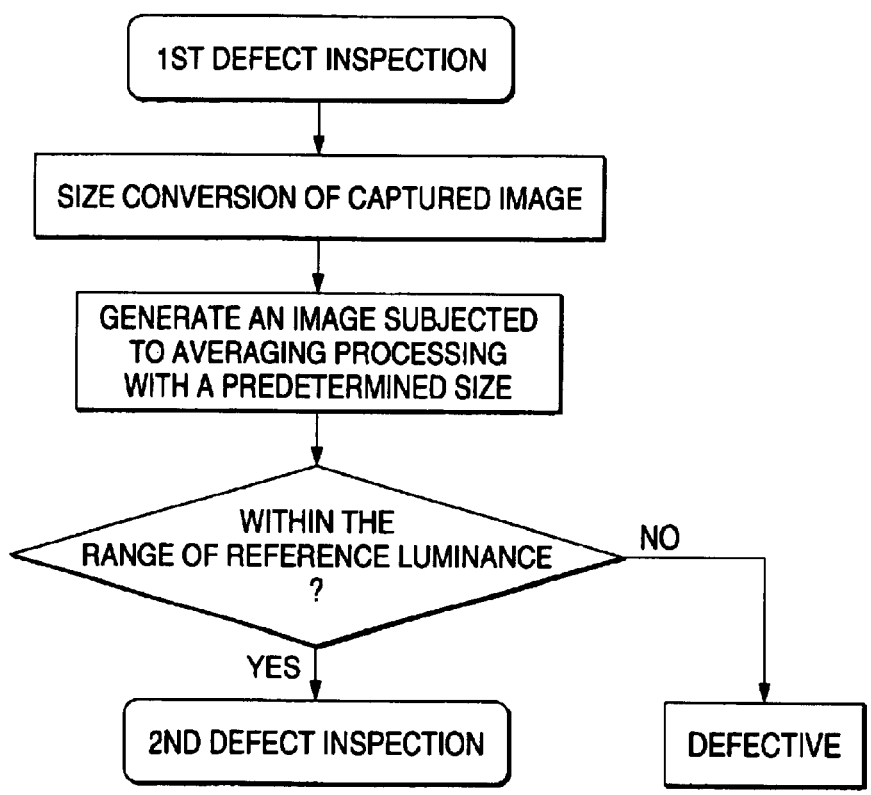
FIG. 5 is a flowchart illustrating the flow of the first defect inspection.
Figure 6:
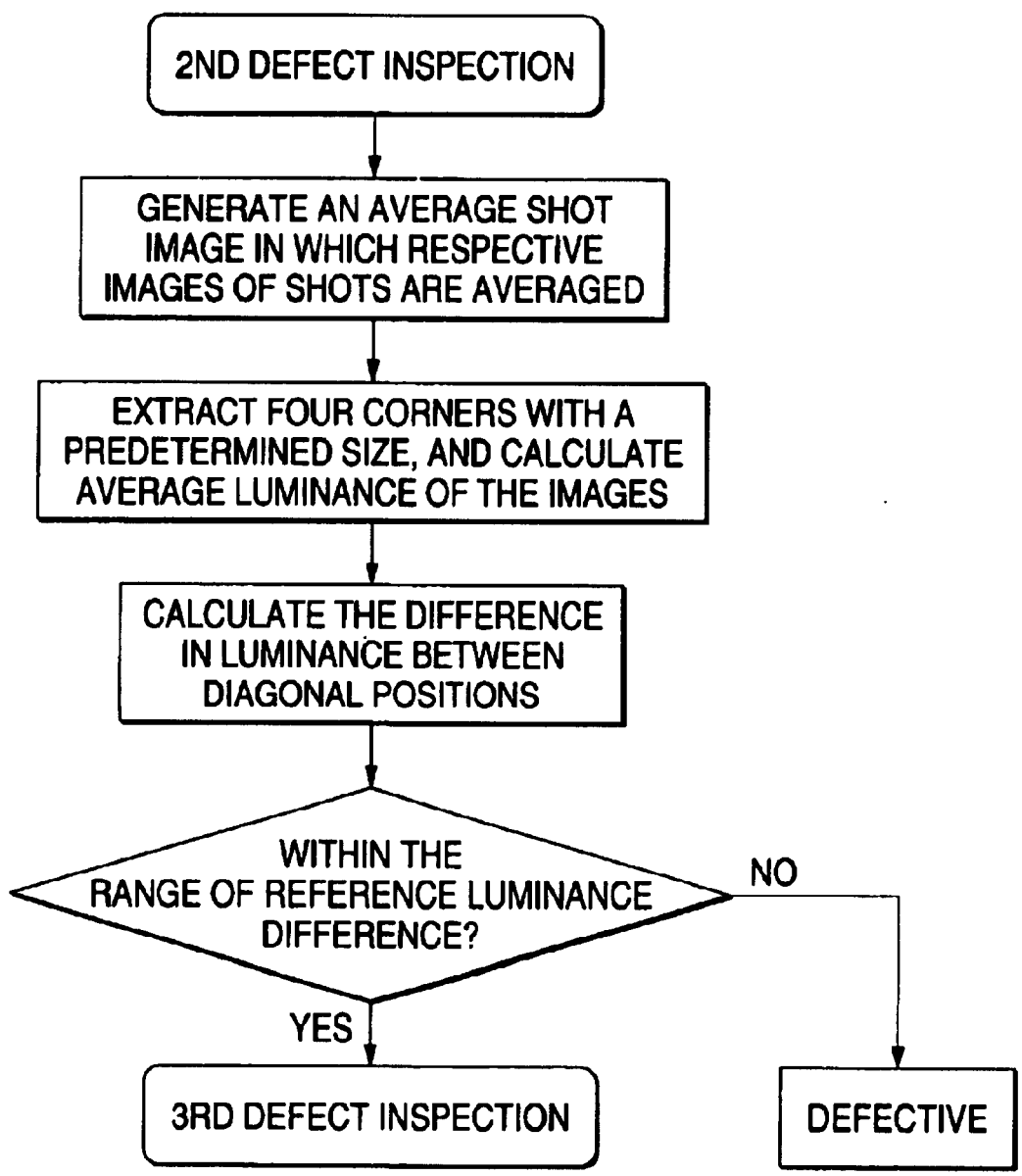
FIG. 6 is a flowchart illustrating the flow of the second defect inspection.
Figure 7:
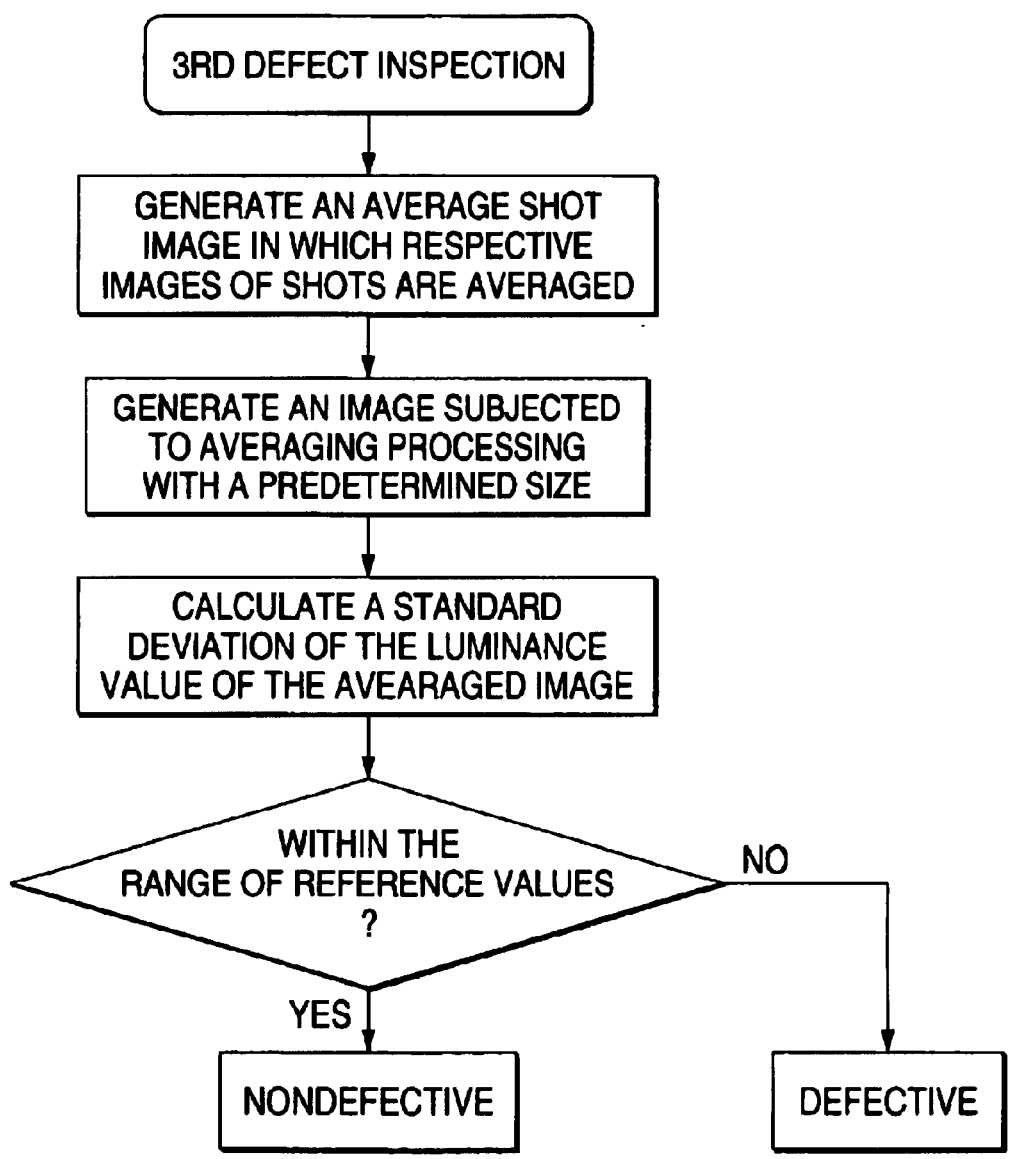
FIG. 7 is a flowchart illustrating the flow of the third defect inspection.

Next, a description will be given of a method of defect inspection using the apparatus. Since there are various types of defects depending on the product type and the manufacturing process, the detection unit 30b detects defects by the three kinds of defect inspection which are described below (refer to the flowcharts in FIGS. 5, 6, and 7) to cope with various defects. Each inspection is performed with respect to each captured image by the bright-field illumination and the dark-field illumination.

First Defect Inspection

The first defect inspection makes it possible to detect defects such as relatively large defects (including scars, dust, etc.), a partial faulty resist, overall faulty surface due to uncoating of the resist, etc. on the wafer W where a chip pattern is formed.

Since various chip patterns are formed on the wafers W depending on the product type and the manufacturing process, in order to perform inspection without a master image, it is necessary to decrease the influence of this chip pattern. In the first inspection, averaging processing which will be described below is performed with a predetermined size; however, since the size of each chip of the chip pattern is not of a size which is an integral multiple of the size of each pixel of the image, it is impossible to sufficiently eliminate the effect of the chip pattern under this condition.

Accordingly, the detection unit 30b performs size conversion process for an original image (captured image)

stored in the memory 30a so that the size of one chip or the size of an integral multiple of the chip assumes the size of substantially an integral multiple of the size of one pixel (so that the two sizes match) and then performs the averaging process. For example, by making a calculation from the chip design drawing of the wafer W, the size conversion process is performed so that the size of one chip assumes the size of 5×5 pixels (so that the two sizes match). Therefore, since the positional relationship between the each chip of chip pattern and each pixel is adjusted, the influence of the chip pattern at the time of averaging processing is decreased. It should be noted that when the chip pattern formed on the wafer W is captured by the above-described optical system, since the size of a normal chip is that of 10×10 pixels or more, the processing speed is accelerated by converting the size of one chip to a smaller size of 5×5 pixels, so that this arrangement is advantageous (however, if the number of pixels of one chip is made excessively smaller, the sensitivity of defect inspection declines, so that the size of 5×5 pixels or thereabouts is preferable).

Next, the averaging processing is performed for the image having predetermined size (averaged size) after the size conversion process. The larger averaged size is advantageous in order to increase the reliability of the data. However, to the contrary, a smaller averaged size is advantageous in order to detect local defects. Accordingly, in this apparatus, an averaged size is so determined that the averaged size is an integral multiple of the size of one chip and is the size of ⅓ to ½ or thereabouts of a shot size of exposure. For example, in the case where one shot comprises 5×5 chips, a region of 2×2 chips is set as the averaged size. However, in the case where one shot comprises one chip, that chip size is used as it is as the averaged size.

Incidentally, in the case where the size conversion process is performed in the preceding step such that the size of an integral multiple of the size of one chip is the size of substantially an integral multiple A (A pixels) of the size of one pixel (so that the two sizes match), this averaged size is set to be the size of A pixels (such that the two sizes match).

A description will be given of the averaging processing. For example, it is assumed that one chip comprises a region of 5×5 pixels and the averaged size is set as this size of 5×5 pixels (to simplify the description, the case of one shot covering one chip is illustrated as an example). As shown in FIG. 2A, an image of a region 1-1 comprising 5×5 pixels is extracted from the image after the size conversion process, and an average value of luminance values of the pixels is determined. This average value is set as the value of a 1-1 coordinate pixel shown in FIG. 2D.

Figure 2B:
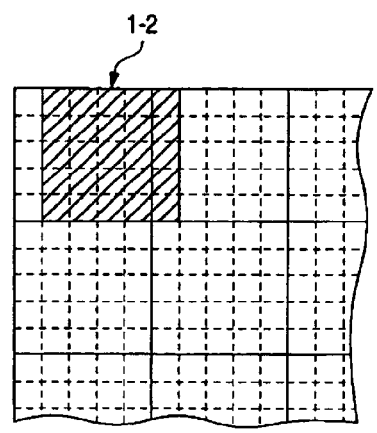
Figure 2C:
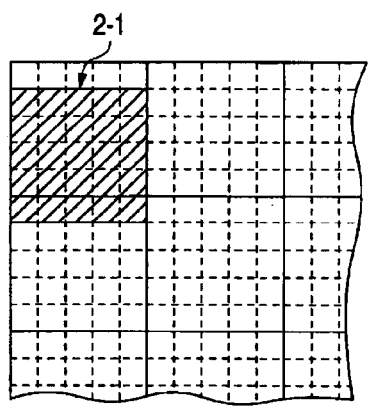
Figure 2D:
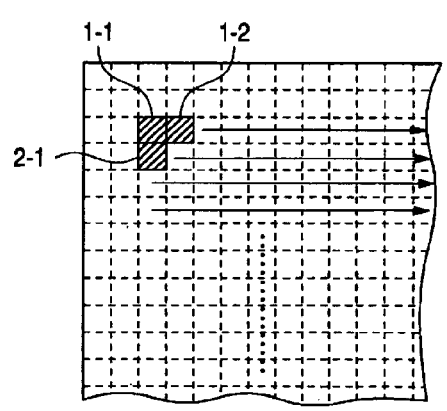

Next, as shown in FIG. 2B, an average value of luminance for a 1-2 region obtained by moving the averaging region by one pixel portion in the rightward direction is determined as described above, and this value is set as a value of a 1-2 coordinate pixel shown in FIG. 2D. This processing is consecutively executed in the rightward direction, and upon completion of this processing up to a right end, an average value of luminance is similarly determined with respect to a 2-1 region obtained by moving the averaging region by one pixel portion in the downward direction from the 1-1 region, as shown in FIG. 2C. The average value at this time is set as a value of the 2-1 coordinate pixel shown in FIG. 2D.

With respect to all the chip regions, the above-described processing is performed by consecutively effecting scanning in the raster direction (from left to right, from top to down), and an averaged image formed by average values of the images extracted with the averaged size is prepared.

Here, the size of the region of the chips included in the averaged size becomes identical in total even if the region of the chips is moved by a one-pixel portion. Accordingly, in the first defect inspection, it is possible to determine whether the inspection object includes defect or not by making a comparison between the value of each pixel of the thus-prepared averaged image and the range of reference average luminance as an inspection condition. That is, in a case where there is a relatively large defect on the wafer W, the average luminance with the averaged size changes, so that the defect can be detected by performing binarization through comparison with the range of reference luminance of the non-defective product level. The range of reference luminance of the non-defective product level can be determined by obtaining in advance an averaged image with respect to a multiplicity of non-defective product samples by similar processing.

In addition, in a case where there is an overall faulty surface such as the uncoating of the resist, since all the values of the averaged image fall outside the range of the inspection condition, the defective state can be detected in this case as well.

Second Defect Inspection

Since the defect due to defocus or an inclination of focus of a stepper sometimes appears as subtle brightness as compared with the unevenness of the film thickness of the resist (the object in this case being the unevenness of the film thickness of the nonefective product level), even if individual shots are individually inspected, inspection with high reliability is difficult. The second defect inspection decreases the influence due to the unevenness of the film thickness (including the unevenness of the substrate) by using an image in which all the shots on one wafer W are averaged, thereby making it possible to detect the defect due to the inclination of the focus of the stepper with high sensitivity.

First, the detection unit 30b extracts all the shot images on the wafer W from an original image (a captured image) stored in the memory 30b, and prepares an average shot image (an image having the same size as the shot size) in which the respective images of the shots are averaged. Since the unevenness of the film thickness of the resist spreads concentrically, if all the shorts are averaged, the brightness due to the unevenness decreases. On the other hand, the brightness due to an abnormality in focusing common to all the shots remains without decreasing even if averaging is effected.

It should be noted that, in the process of generating the average shot image, the processing of this average shot image may be carried out after size conversion is performed so that the size of one shot assumes the size of substantially an integral multiple of one pixel (so that the two sizes match) in the same way as the first defect inspection. If the average shot image is generated without performing the size conversion, the average shot image becomes moderately blurred due to the distortion of the optical system and the mismatch between the size of the chip and the size of the pixels. Hence, even if next processing is performed in this state, no hindrance is caused in the practical use.

Figure 3:
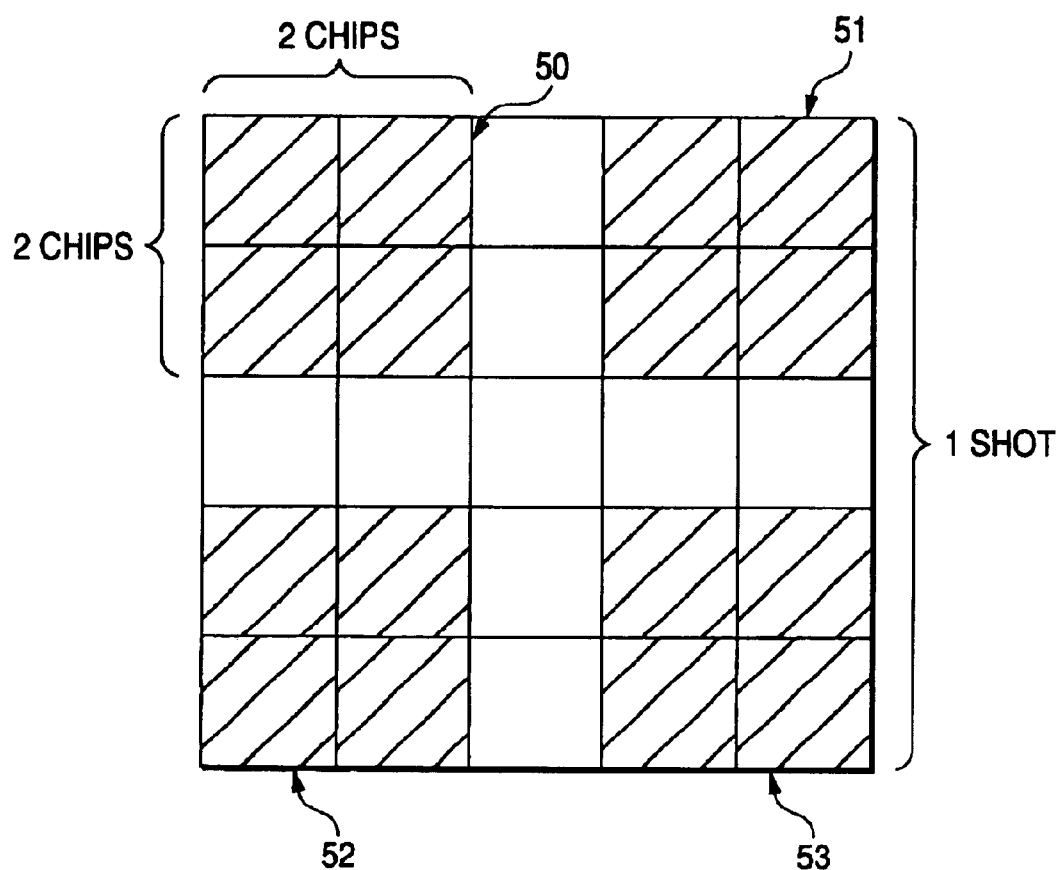
FIG. 3 is a diagram illustrating an example in which images at four corners are extracted from an average shot image in a second defect inspection.

Next, four corners of the average shot image, each of which has a size smaller than the size of one shot, are extracted. In this apparatus, images are extracted with the size of ⅓ to ½ or thereabouts of one integral multiple of the size of one chip or the size of one shot. Subsequently, the average luminance of the extracted images is calculated. In this case as well, the size for calculating the average luminance is preferably set to the size of ⅓ to ½ or thereabouts of the size of one shot for the same reason as that of the above-described first defect inspection. For example, in the case where one shot comprises 5×5 chips, as shown in FIG. 3, four images 50, 51, 52, and 53 each comprising 2×2 chips and positioned at the corner are extracted, and the average luminance of each image is calculated. However, in the case of one shot covering one chip, since calculation cannot be made in the unit of chips, average luminance is calculated with respect to the images at four corners extracted with the size of ⅓ to ½ or thereabouts of the size of one shot for convenience's sake.

In the case where the focus of the stepper is inclined, the four corners of the shot suffer the greatest influence therefrom. Therefore, the difference of the average luminance at diagonal positions of the four corners obtained as above is made use of in the detection of the inclination of focusing. In the example shown in FIG. 3, the respective differences in the average luminance between the images 50 and 53 and between the images 51 and 52 are calculated. A determination of the defective or nondefective state of the wafer W can be made depending on whether or not each of these differences is within the range of the reference average luminance difference set in advance as the inspection condition. If the differences fall outside the range of the inspection condition, it is determined that the case is that of the overall faulty surface.

Third Defect Inspection

In the third defect inspection, an image in which all the shots are averaged is used in the same way as the second defect inspection, thereby making it possible to detect defects due to the defocusing of the stepper with high sensitivity.

In the same way as the second defect inspection, all the shot images on the wafer W are extracted, and an average shot image in which the respective images of the shots are averaged is generated. Next, averaging processing is performed for this average shot image with a predetermined averaged size, so that an averaged image of the average shot image is obtained. With respect to the averaged size in this case as well, images are extracted with a size smaller than the size of one shot, and it is preferable to use an averaged size which is an integral multiple of the size of one chip so as to be the size of ⅓ to ½ or thereabouts of the size of one shot. In the case of one shot covering one chip, since the averaged image consists of one pixel and the calculation cannot be made, averaging processing is performed in a similar manner with the size of ⅓ to ½ or thereabouts of the size of one shot for convenience's sake.

In the case of slight defocusing, generally, the average luminance changes, so that detection is possible by the first defect inspection. However, in a case where large defocusing occurs, there are cases where the average luminance becomes similar to that of a nondefective product, so that the use of the first defect inspection alone is insufficient. In this case, since it is possible to make use of the phenomenon in which the brightness due to the aberrations of the exposure optical system of the stepper becomes noticeable or extremely small due to the defocusing, in the third defect inspection, the degree of variation of the luminance of the averaged image prepared by subjecting the average shot image to further averaging processing in the above-described manner is calculated. In this apparatus, a standard deviation is used in the calculation of the degree of variation of luminance.

Figure 4A:
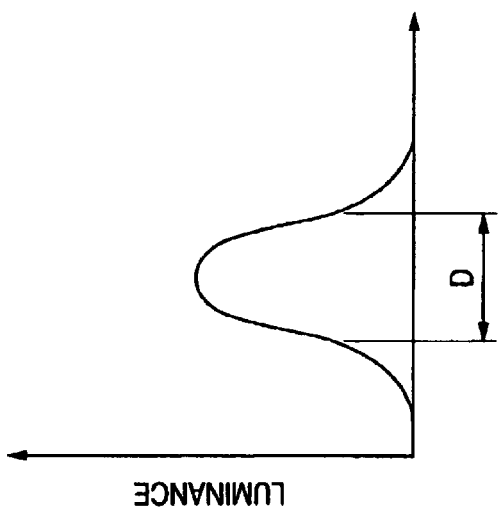
FIGS. 4A to 4C are histograms illustrating the distribution of the luminance of averaged images in a third defect inspection.
Figure 4B:
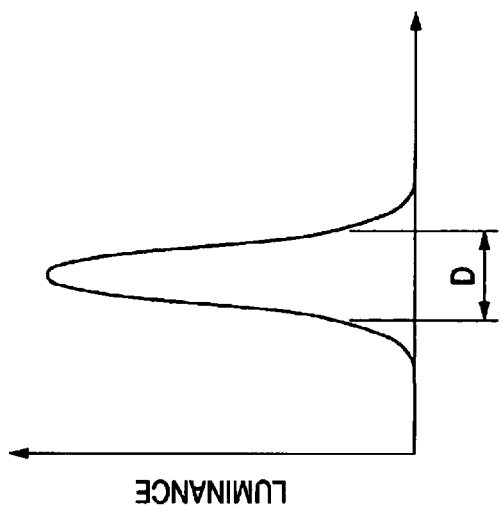
Figure 4C:
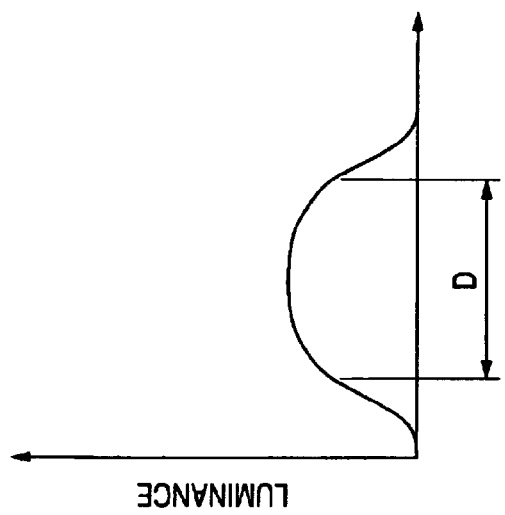

FIG. 4A shows an example in which the distribution of the luminance of an averaged image in a nondefective sample is shown by a histogram. In a case where large defocusing occurs, and brightness due to noticeable aberrations occurs in the shots, the distribution of luminance becomes as shown in FIG. 4C. In a case where brightness due to aberrations practically disappears, the distribution of luminance becomes as shown in FIG. 4B. In these distribution in FIGS. 4B and 4C, the standard deviation of the luminance of the averaged image appears to be substantially different from the width D shown in FIG. 4A. Accordingly, if the standard deviation of the luminance of the averaged image is calculated, and a determination of the defective or nondefective state can be made depending on whether the value of the calculated standard deviation is within the range of the reference values of the inspection condition. If the value falls outside the range of the inspection condition, a determination is made that the case is that of the overall faulty surface.

The above-described first to third defect inspections are respectively performed with respect to the captured images by bright-field illumination and the captured images by dark-field illumination. In the bright-field illumination, white illumination light is mainly used; however, there are types of wafers W in which defects can be detected more easily if the wavelength of the illumination light is changed, in which this case illumination is effected by selecting an appropriate wavelength by the filter 4.

As described above, since the inspection condition in each inspection is simple numerical data, the amount of data stored in the detection unit 30b can be far smaller than the master image. This is particularly advantageous in the case where a multiplicity of types of wafers are inspected. Even in a case where there are a plurality of inspection apparatuses, the inspection standard of the same numerical data can be used for the wafers of the same type, and since a master image is not required, the management of the apparatuses is facilitated In addition, inspection can be performed by an image in which the overall surface of the wafer has been imaged, and image processing is simple, so that inspection can be performed at high speed.

As described above, in accordance with the invention, it is possible to detect defects at high speed without using a master image.

What is claimed is:

1. A defect inspection method of inspecting a defect of an inspection object having a chip pattern, the defect inspection method comprising the steps of:
   inputting a captured first image of the inspection object;
   converting the inputted first image to a second image so that a first size of an integral multiple of a size of a chip matches a second size of a substantially integral multiple of a size of a pixel;
   generating an averaged image having the second size by averaging the converted second image;
   determining a luminance of the generated averaged image; and
   detecting the defect based on the determined luminance of the generated averaged image and a predetermined reference luminance.

2. A defect inspection method of inspecting a defect of an inspection object having a chip pattern, the defect inspection method comprising the steps of:
   inputting a captured first image of the inspection object;
   extracting second images of each exposure shot from the inputted first image;
   generating an average shot image by averaging the extracted second images;
   extracting third images at four corners of the generated average shot image, each of the third images having a first size smaller than a size of the exposure shot;
   determining a luminance of each third image, respectively;

determining a difference in the determined luminance between two of the third images which are in diagonal position; and detecting the defect based on the determined difference in the determined luminance and a predetermined reference luminance difference.

3. The defect inspection method according to claim 2, wherein the first size includes at least one of a size of an integral multiple of a size of a chip and a size of substantially ⅓ to ½ of the size of the exposure shot.

4. A defect inspection method of inspecting a defect of an inspection object having a chip pattern, the defect inspection method comprising the steps of:

inputting a captured first image of the inspection object;

extracting second images of each exposure shot from the inputted first image;

generating an average shot image by averaging the extracted second images;

generating an averaged image by averaging the generated average shot image, the generated averaged image having a first size of an integral multiple of a size of a chip, the first size being smaller than a size of the exposure shot;

determining a luminance of the generated averaged image;

determining a standard deviation of the determined luminance of the generated averaged image; and detecting the defect based on the determined standard deviation of the determined luminance and a predetermined reference luminance standard deviation.

5. The defect inspection method according to claim 4, wherein the first size is a size of substantially ⅓ to ½ of the size of the exposure shot.

6. A defect inspection apparatus for inspecting a defect of an inspection object having a chip pattern, the defect inspection apparatus comprising:

an inputting unit which inputs a captured first image of the inspection object; and an image processor which detects the defect according to a program stored therein, the program including the steps of:

converting the inputted first image to a second image so that a first size of an integral multiple of a size of a chip matches a second size of a substantially integral multiple of a size of a pixel, generating an averaged image having the second size by averaging the converted second image, determining a luminance of the generated averaged image, and detecting the defect based on the determined luminance of the generated averaged image and a predetermined reference luminance.

7. A defect inspection apparatus for inspecting a defect of an inspection object having a chip pattern, the defect inspection apparatus comprising:

an inputting unit which inputs a captured first image of the inspection object; and an image processor which detects the defect according to a program stored therein, the program including the steps of:

extracting second images of each exposure shot from the inputted first image, generating an average shot image by averaging the extracted second images, extracting third images at four corners of the generated average shot image, each of the third images having a first size smaller than a size of the exposure shot, determining a luminance of each third image, respectively, determining a difference in the determined luminance between two of the third images which are in diagonal position, and detecting the defect based on the determined difference in the determined luminance and a predetermined reference luminance difference.

8. The defect inspection apparatus according to claim 7, wherein the first size includes at least one of a size of an integral multiple of a size of a chip and a size of substantially ⅓ to ½ of the size of the exposure shot.

9. A defect inspection apparatus for inspecting a defect on an inspection object having a chip pattern, the defect inspection apparatus comprising:

an inputting unit which inputs a captured first image of the inspection object; and an image processor which detects the defect according to a program stored therein, the program including the steps of:

extracting second images of each exposure shot from the inputted first image, generating an average shot image by averaging the extracted second images, generating an averaged image by averaging the generated average shot image, the generated averaged image having a first size of an integral multiple of a size of a chip, the first size being smaller than the size of the exposure shot, determining a luminance of the generated averaged image, determining a standard deviation of the determined luminance of the generated averaged image, and detecting the defect based on the determined standard deviation of the determined luminance and a predetermined reference luminance standard deviation.

10. The defect inspection apparatus according to claim 9, wherein the first size is a size of substantially ⅓ to ½ of the size of the exposure shot.

* * * * *